(12) United States Patent
Ramel et al.

(10) Patent No.: US 8,574,919 B2
(45) Date of Patent: Nov. 5, 2013

(54) MECHANICAL CARTRIDGE WITH TEST STRIP FLUID CONTROL FEATURES FOR USE IN A FLUID ANALYTE METER

(75) Inventors: Urs A. Ramel, Sunnyvale, CA (US); Dillan Tay, San Jose, CA (US)

(73) Assignee: Bayer HealthCare LLC, Tarrytown, NY (US)

( * ) Notice: Subject to any disclaimer, the term of this patent is extended or adjusted under 35 U.S.C. 154(b) by 392 days.

(21) Appl. No.: 12/661,022

(22) Filed: Mar. 8, 2010

(65) Prior Publication Data

US 2010/0226822 A1 Sep. 9, 2010

Related U.S. Application Data

(63) Continuation of application No. 11/121,972, filed on May 4, 2005, now Pat. No. 7,674,615.

(60) Provisional application No. 60/568,293, filed on May 4, 2004.

(51) Int. Cl.
*G01N 21/75* (2006.01)

(52) U.S. Cl.
USPC ........... 436/164; 436/174; 436/177; 436/178; 436/180; 436/165

(58) Field of Classification Search
USPC .................. 436/164, 165, 174, 177, 178, 180
See application file for complete search history.

(56) References Cited

U.S. PATENT DOCUMENTS

| 4,761,381 | A | | 8/1988 | Blatt et al. |
| 5,114,350 | A | * | 5/1992 | Hewett ................. 435/286.4 |
| 5,208,163 | A | | 5/1993 | Charlton et al. |
| 5,885,527 | A | | 3/1999 | Buechler |
| 5,912,134 | A | | 6/1999 | Shartle |
| 5,962,333 | A | | 10/1999 | Incorvia et al. |
| 5,997,817 | A | | 12/1999 | Crismore et al. |
| 6,084,660 | A | | 7/2000 | Shartle |
| 6,087,184 | A | | 7/2000 | Magginetti et al. |
| 6,143,164 | A | | 11/2000 | Heller et al. |

(Continued)

FOREIGN PATENT DOCUMENTS

| EP | 1486766 | 12/2004 |
| JP | 07-055809 | 3/1995 |

(Continued)

OTHER PUBLICATIONS

Office Action from Japanese Pantet Application No. 2007-511573, dated Jan. 26, 2011.

(Continued)

*Primary Examiner* — Melanie Y Brown
(74) *Attorney, Agent, or Firm* — Lerner, David, Littenberg, Krumholz & Mentlik, LLP

(57) ABSTRACT

A structure for controlling fluid flow from a sample receiving pad into a lateral flow assay test strip, including: a lateral flow assay test strip; a sample pad abutting the lateral flow assay test strip; a pinch wall positioned to direct fluid flow from the sample pad to the lateral flow assay test strip; a top support structure positioned on top of the test strip; and a bottom support structure positioned underneath the test strip, wherein each of the top and bottom support structures comprise a plurality of separate spaced-apart support ribs positioned along the length of the test strip.

12 Claims, 6 Drawing Sheets

(56) References Cited

U.S. PATENT DOCUMENTS

| | | |
|---|---|---|
| D438,310 S | 2/2001 | Yamanishi et al. |
| 6,296,020 B1 | 10/2001 | McNeely et al. |
| 6,297,020 B1 | 10/2001 | Brock |
| 6,319,466 B1 | 11/2001 | Markovsky et al. |
| D456,082 S | 4/2002 | Bouse et al. |
| 6,372,516 B1 * | 4/2002 | Sun ............................... 436/518 |
| 6,426,230 B1 | 7/2002 | Feistel |
| D468,437 S | 1/2003 | McMenamy et al. |
| 6,521,182 B1 | 2/2003 | Shartle et al. |
| 6,572,745 B2 | 6/2003 | Rappin et al. |
| 6,652,814 B1 | 11/2003 | House et al. |
| 6,755,949 B1 | 6/2004 | Bhullar et al. |
| 6,767,510 B1 | 7/2004 | Buechler |
| D500,142 S | 12/2004 | Crisanti et al. |
| 6,830,936 B2 | 12/2004 | Anderson et al. |
| 6,846,453 B1 | 1/2005 | Uesaka et al. |
| 6,901,963 B2 | 6/2005 | Kim et al. |
| 6,905,882 B2 | 6/2005 | Buechler |
| 6,908,593 B1 | 6/2005 | Shartle |
| 6,919,046 B2 | 7/2005 | O'Connor et al. |
| 6,935,772 B2 | 8/2005 | Karp et al. |
| D512,512 S | 12/2005 | Bell et al. |
| D530,826 S | 10/2006 | Rich et al. |
| 7,241,417 B2 * | 7/2007 | Lee et al. ...................... 422/408 |
| 7,674,615 B2 * | 3/2010 | Ramel et al. ............... 435/286.5 |
| 2002/0061260 A1 | 5/2002 | Husar |
| 2002/0146346 A1 | 10/2002 | Konecke |
| 2003/0157724 A1 | 8/2003 | Petrich et al. |
| 2004/0028558 A1 | 2/2004 | Pollock et al. |
| 2005/0227370 A1 | 10/2005 | Ramel et al. |
| 2009/0136963 A1 * | 5/2009 | Breidenthal et al. .............. 435/6 |
| 2010/0226822 A1 | 9/2010 | Ramel et al. |

FOREIGN PATENT DOCUMENTS

| | | |
|---|---|---|
| JP | 2000-356638 A | 12/2000 |
| JP | 2002-509605 T | 3/2002 |
| JP | 5178190 | 4/2013 |
| WO | 9406013 A1 | 3/1994 |

OTHER PUBLICATIONS

Supplementary European Search Report for Application No. EP05746988 dated May 30, 2012.

Korean Office Action for Application No. 10-2012-7024768 dated Nov. 9, 2012.

* cited by examiner

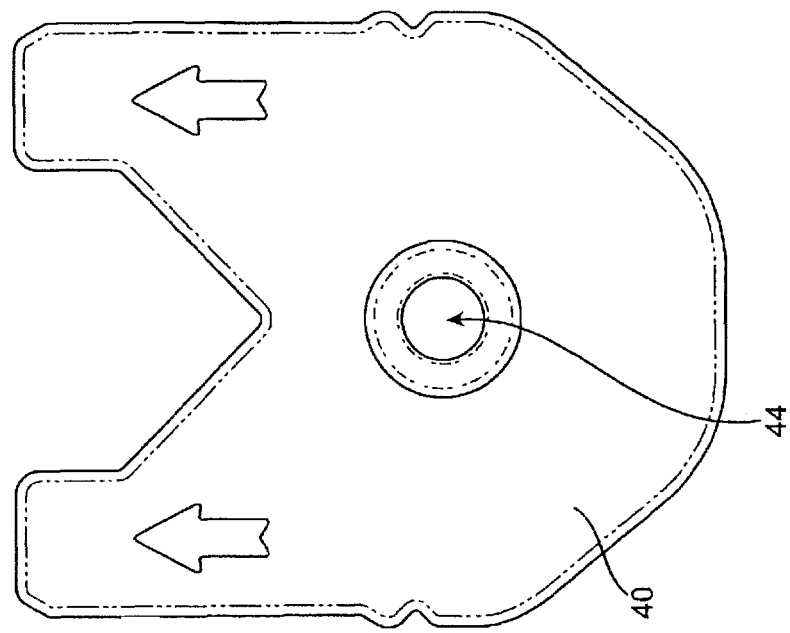
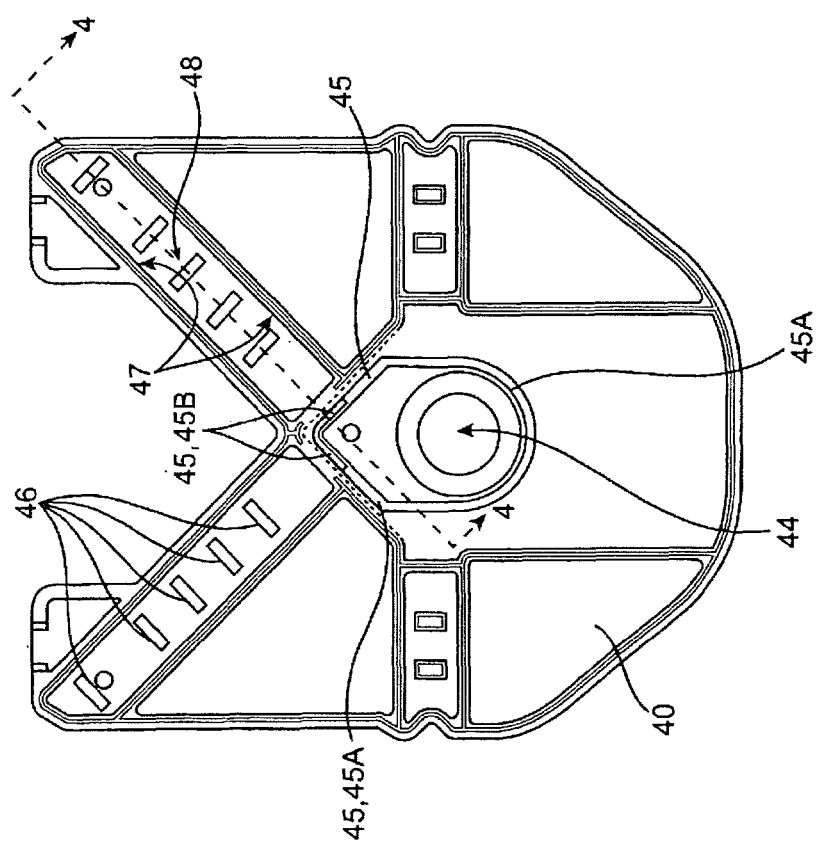

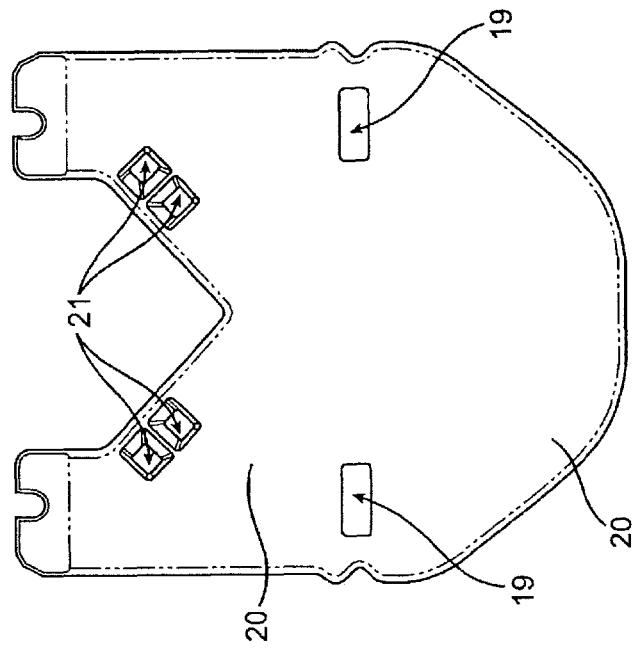
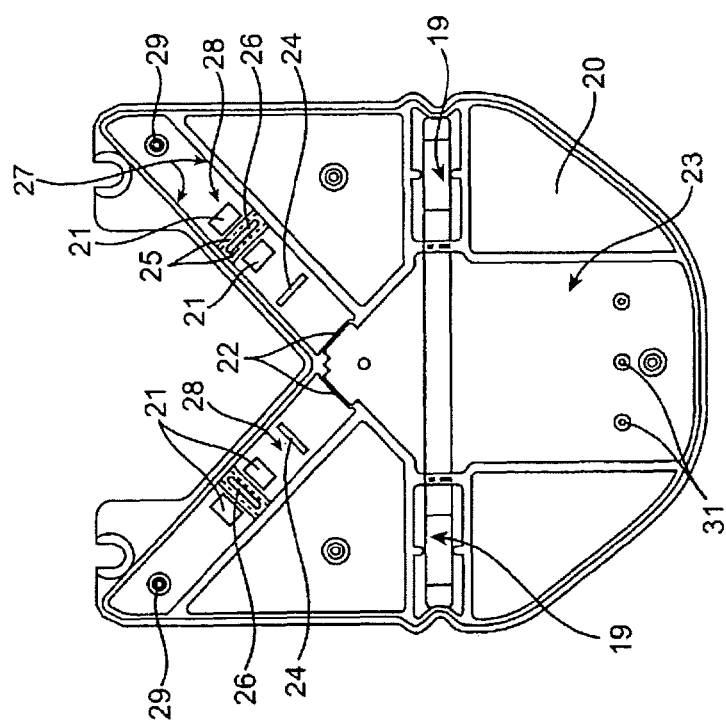
FIG. 3A
FIG. 3B

MECHANICAL CARTRIDGE WITH TEST STRIP FLUID CONTROL FEATURES FOR USE IN A FLUID ANALYTE METER

CROSS-REFERENCE TO RELATED APPLICATIONS

This application is a continuation of U.S. patent application Ser. No. 11/121,972, filed May 4, 2005 now U.S. Pat. No. 7,674,615, which claims the benefit of the filing date of U.S. Provisional Application No. 60/568,293, filed May 4, 2004, the disclosures of which applications are hereby incorporated by reference herein.

TECHNICAL FIELD

The present invention relates to systems for improving fluid flow through lateral flow assay test strips. The present invention also relates to disposable cartridges used in fluid analyte test meters.

BACKGROUND OF THE INVENTION

Lateral flow assay test strips are widely used in a variety of different applications. The most common problem with using lateral flow assay test strips is ensuring an optimal amount of fluid sample flows therethrough. Specifically, it is important to ensure that the test strip receives enough fluid such that it is fully saturated (so that fluid flows fully through the length of the test strip). However, it is also important that the test strip not be flooded (such that fluid may seep away from the test strip by capillary action, thereby reaching other parts of the interior of the device).

Moreover, it is also desirable that the fluid sample passes through the test strip as a uniform front without advancing faster along either the sides or the middle of the test strip. Furthermore, a common problem with lateral flow assay test strips is that fluid may flow (or simply gather) along the top or bottom surfaces of the test strip (thus partially bypassing the reaction occurring within the test strip itself). Lastly, fluid samples may splash onto the test strip from a sample receiving pad, producing undesirable results. Specifically, such splashing onto the test strip may result in flooding (with capillary flow away from the test strip).

In accordance with the present invention, a system is provided for supporting a test strip for use in a fluid analyte meter such that fluid flow is controlled both as fluid initially enters the test strip from a sample pad, and also as the fluid moves through the test strip itself. Thus, the present system overcomes the above identified disadvantages that are common to many existing lateral flow assay handling systems.

SUMMARY OF THE INVENTION

In one aspect, the present flow control system is positioned within a disposable cartridge that houses at least one lateral flow assay test strip. The disposable cartridge is received into a re-useable fluid analyte test meter, with the meter then reading the results of the assay reaction that is carried out within the lateral flow assay test strip(s).

In accordance with the present invention, the disposable mechanical cartridge includes fluid control features that assist in controlling fluid flow movement from a sample receiving pad into a test strip in a desired manner, maintaining appropriate saturation of the test strip, but without flooding the test strip. Additionally, the disposable mechanical cartridge includes fluid control features that support the test strip in a manner that assists in controlling fluid flow movement through the test strip itself. Specifically, the present fluid control features ensure that fluid flow occurs laterally through the test strip, while preventing capillary fluid flow along the top or bottom surfaces of the test strip, and while preventing fluid from seeping away from the test strip and into other locations in the cartridge housing. In addition, in the case of test strips with sections made of different materials, the present fluid control features can advantageously be used to hold overlapping portions of the test strip together in uniform contact, thereby facilitating fluid transfer between the various material portions of the test strip.

In one aspect, the present fluid control system includes a lateral flow assay test strip; a sample pad abutting the lateral flow assay test strip; and a pinch wall positioned to direct fluid flow from the sample pad to the lateral flow assay test strip.

In one exemplary embodiment, the pinch wall is positioned to compress the sample receiving pad. The pinch wall may include: a first portion separating a sample receiving portion of the sample receiving pad from a portion of the sample pad positioned adjacent to the test strip, and a second portion separating the sample receiving portion of the sample pad from a portion of the sample pad positioned away from the test strip. In accordance with the present invention, the first portion of the pinch wall compresses the sample receiving pad to a lesser degree than the second portion of the sample receiving pad.

As will be explained, an advantage of the present pinch wall is that it directs an initial portion of the sample received on the sample pad toward the test strip(s), and then directs an excess portion of the sample flow received on the sample pad away from the test strip(s).

In one exemplary embodiment, the first and second portions of the pinch wall may together continuously surround the sample receiving portion of the sample receiving pad. The pinch wall preferably compresses the sample receiving pad such that fluid received onto the sample pad preferentially tends to flow from the sample receiving portion of the sample receiving pad into the portion of the sample pad positioned adjacent to the test strip, and then less so from the sample receiving portion of the sample receiving pad to the portion of the sample pad positioned away from the test strip. Stated another way, the pinch wall preferably compresses the sample receiving pad such that fluid received onto the sample pad will flow more rapidly from the sample receiving portion of the sample receiving pad into the portion of the sample pad positioned adjacent to the test strip, and more slowly from the sample receiving portion of the sample receiving pad to the portion of the sample pad positioned away from the test strip.

In another aspect, the present fluid control system includes a lateral flow assay test strip support system configured to direct flow through a test strip while preventing capillary flow away from the test strip. Specifically, this system may include: a lateral flow assay test strip; a top support structure positioned to compress the test strip; and a bottom support structure positioned underneath the test strip. Each of the top and bottom support structures preferably comprise a plurality of separate spaced-apart support ribs positioned along the length of the test strip. Optionally, the support ribs extend transversely across the test strip. Optionally as well, each of the plurality of support ribs in either the top or bottom supports may be pedestals that do not extend beyond the sides of the test strip.

An advantage of these fluid flow control features is that they promote an even lateral flow through the test strip. That is, the fluid does not tend to advance faster or slower along the edges of the test strip (as compared to the middle of the test strip). In addition, the present fluid flow control features inhibit capillary fluid flow along the top or bottom surfaces of the test strip. (Such flow would vary the surface reflectance of the test strip, thereby altering the test readings).

In another aspect, the fluid control system includes a structure for controlling fluid flow in a lateral flow assay test strip, including: a lateral flow assay test strip having a first portion made of a first material and a second portion made of a second material, wherein an end of the first portion overlaps an end of the second portion; a first supporting rib extending across the overlapping ends of the first and second portions of the lateral flow assay test strip; and a second supporting rib extending across an opposite side of the overlapping ends of the first and second portions of the lateral flow assay test strip.

In another aspect, the present invention provides a disposable cartridge for use in a fluid analyte meter, including: a housing having at least one optical interrogation aperture; a sample receiving pad in the housing; a lateral flow assay test strip adjacent to the optical interrogation aperture; and a moisture barrier in the housing, wherein the moisture barrier prevents moisture from entering the housing, and wherein the moisture barrier covers the optical interrogation aperture, thereby permitting optical interrogation of the test strip therethrough.

The present invention can be used with lateral flow assay test strips as found in various assay meters and body fluid assay metering systems. In only one preferred embodiment, the present system is used in a hemoglobin A1c (HbA1c) meter. In various aspects of the present invention, a drop of blood to be analyzed is placed into the meter, or into the cartridge that is then received into the meter.

BRIEF DESCRIPTION OF THE DRAWINGS

FIG. 2A is a top plan view of the top of the disposable cartridge of FIG. 1.

FIG. 2B is a bottom plan view of the top of the disposable cartridge of FIG. 1.

FIG. 3A is a bottom plan view of the bottom of the disposable cartridge of FIG. 1.

FIG. 3B is a top plan view of the bottom of the disposable cartridge of FIG. 1.

DETAILED DESCRIPTION OF THE DRAWINGS

The present invention provides fluid flow control features for handling fluid flow into, and through, lateral flow assay test strips. As illustrated herein, the present invention is ideally suited for use in disposable cartridges that are inserted into the fluid analyte test meter. in one exemplary use, the present cartridge and test strips are configured for use in measuring hemoglobin A1c (HbA1c). It is to be understood, however, that the present invention is not so limited. For example, it may also be used for detecting other analytes in other fluid samples. As understood herein, the term, body fluid analyte, is taken to mean any substance of analytical interest, such as hemoglobin A1c, cholesterol, triglycerides, albumin, creatinmne, human chorionic gonaotropin (hCG), or the like, in any body fluid, such as blood, urine, sweat, tears, or the like, as well as fluid extracts of body tissues, whether applied directly to the present invention or as a diluted solution. In addition, the present fluid control features may also be used within a disposable single use meter (i.e.: a fluid analyte meter having the sample receiving pad test strip(s) and the present fluid control features therein).

Figure 1:
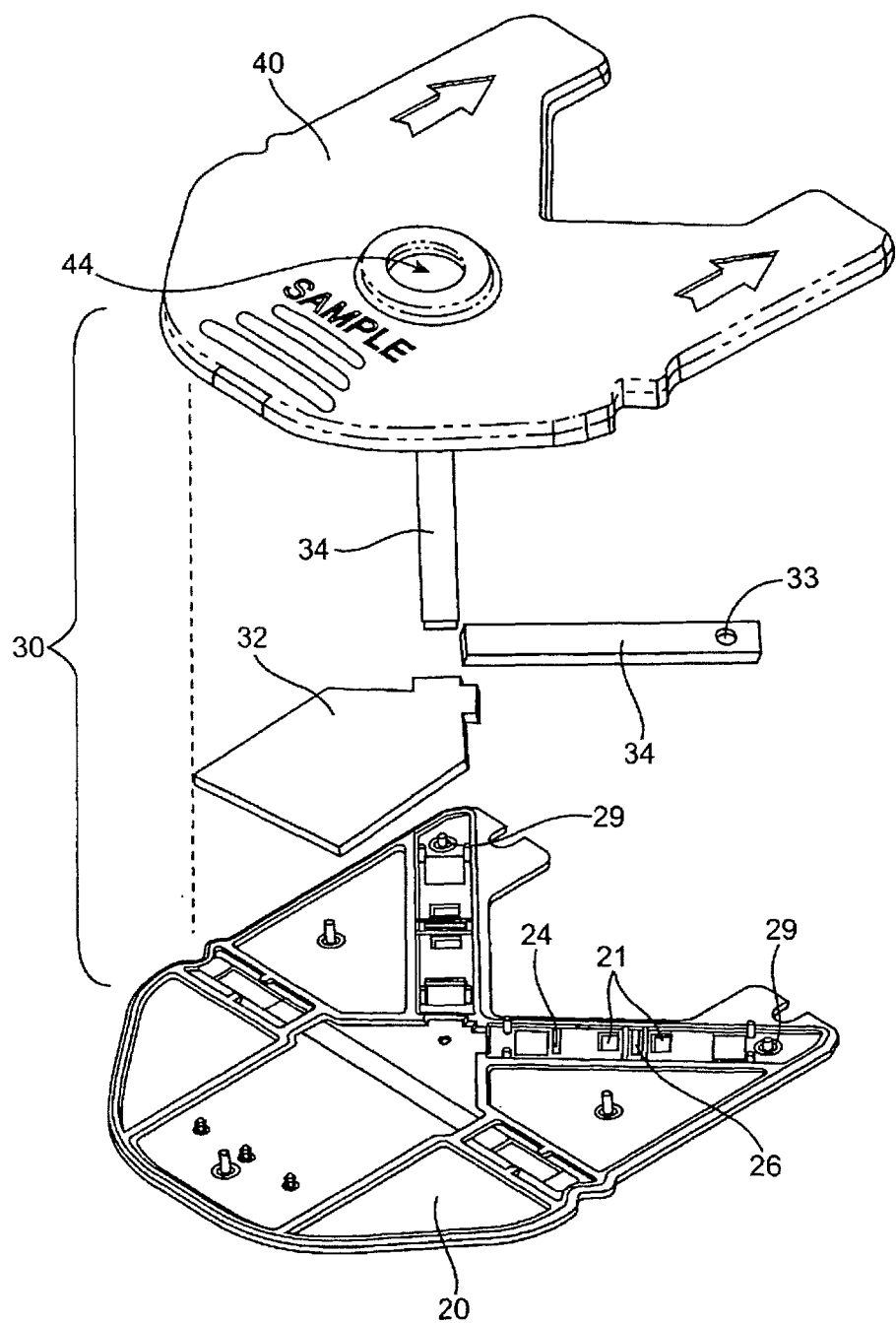
FIG. 1 is an exploded perspective view of a disposable cartridge housing a sample pad and two test strips.

As seen in FIG. 1, a disposable cartridge 30 is provided. Cartridge 30 has a top 40 and a bottom 20, which are placed together such that they sandwich a sample pad 32 and two lateral flow assay test strips 34 therebetween. It is to be understood that the design of cartridge 30 is merely exemplary. Thus, the present invention also covers additional designs including systems with only one, or more than two, test strips 34 therein.

In operation, a fluid sample is introduced into cartridge 30 through a sample receiving top hole 44 in top 40. The fluid sample may be a drop of blood, but is not so limited. The sample is first received onto a sample receiving pad 32. From there, the fluid sample wicks onto test strips 34. A chemical reaction then occurs within each of test strips which may be detected optically by a meter (not shown) through optical interrogation apertures 21 in bottom 20. In preferred embodiments, test strips 34 are lateral flow assay test strips and the reaction that occurs thereon are measured by an optical system (e.g.: reflectometers) in the meter. Examples of such systems are found in U.S. Pat. Nos. 5,837,546; 5,945,345 and 5,580,794, incorporated herein by reference in their entirety for all purposes.

The present fluid control features assist in controlling fluid movement both: (a) from sample receiving pad 32 onto test strips 34 and (b) through test strips 34. These fluid control features, and their respective advantages, will be described fully below.

FIGS. 2A and 213 show further details of top 40, as follows. As stated above, top 40 has a hole 44 through which a fluid sample is introduced. A pinch wall 45 extends downwardly from top 40, having a first portion 45A and a second portion 45B. Pinch wall 45 is positioned to sit directly on top of sample receiving pad 32. First portion 45A extends downwardly a greater distance from top 40 than second portion 45B extends downwardly from top 40. (IE: pinch wall portion 45A has a greater height than pinch wall portion 45B). As a result, when top 40 and bottom 20 are placed together, first portion 45A compresses sample pad 32 more than second portion 45B compresses sample pad 32. Together, portions 45A and 45B may comprise a continuous wall around hole 44, as shown. As will be explained with reference to FIG. 4 below, this feature is used to advantageously control fluid flow movement from sample pad 32 onto test strips 34.

In accordance with the illustrated embodiments, the pinch wall is positioned on top of the sample pad. However, the present invention is not so limited. For example, it is to be understood that the pinch wall may instead be positioned below the sample pad. Alternatively, systems where pinch walls are positioned both above and below the sample pad are contemplated within the scope of the present invention.

In addition, top 40 further includes a plurality of downwardly projecting support ribs 46. Support ribs 46 are positioned on top of test strips 34 when top 40 and bottom 20 are placed together. Support ribs 46 extend transversely across test strips 34. As will be explained with reference to FIG. 4 below, support ribs 46 are used to assist in advantageously controlling fluid flow through test strips 34.

As can be seen, support ribs 46 may preferably be in the form of pedestals (i.e.: the side edges of support ribs 46 do not contact the side edges 47 of chamber 48,) In one exemplary embodiment, the width of support ribs 46 does not exceed the width of test strips 34. Thus, transverse support ribs 46 do not extend beyond the sides of test strips 34.

FIGS. 3A and 3B show further details of bottom 20, as follows. Bottom 20 has a sample pad receiving portion 23 (into which sample pad 32 is placed). In addition, bottom 20 has a pair of chambers 28 in which test strips 34 are received. Bottom 20 has three pairs of spaced-apart ribs 22, 24 and 26. Test strips 34 are positioned on top of support ribs 24 and 26. Ribs 22 are positioned against an end of sample receiving pad 32, adjacent to where sample receiving pad 32 contacts each of test strips 34. Support ribs 24 and 26 may be pedestals, as shown (i.e.: the side edges of support ribs 24 and 26 do not contact the side edges 27 of chambers 28.) In one exemplary embodiment, the width of support ribs 24 and 26 does not exceed the width of test strips 34. Thus, transverse support ribs 24 and 26 do not extend beyond the sides of test strips 34. In one embodiment, a pair of recesses 25 may be disposed on either side of support rib 26. This design is particularly advantageous in that recesses 25 provide isolation on either side of support rib 26 such that capillary fluid flow away from test strip 34 at this location is inhibited.

Additionally, pins 29 may be provided to anchor one end of test strips 34. Specifically, pins 29 are received into each of holes 33 in test strip 34 (FIG. 1). Further details of each of ribs 22, 24 and 26 will be illustrated with respect to FIG. 4, below.

Additionally, a plurality of sample pad forward biasing pins 31 can be provided at the rear end of sample pad 32 to ensure that sample pad 32 does not move about in sample pad receiving portion 23.

Figure 3C:
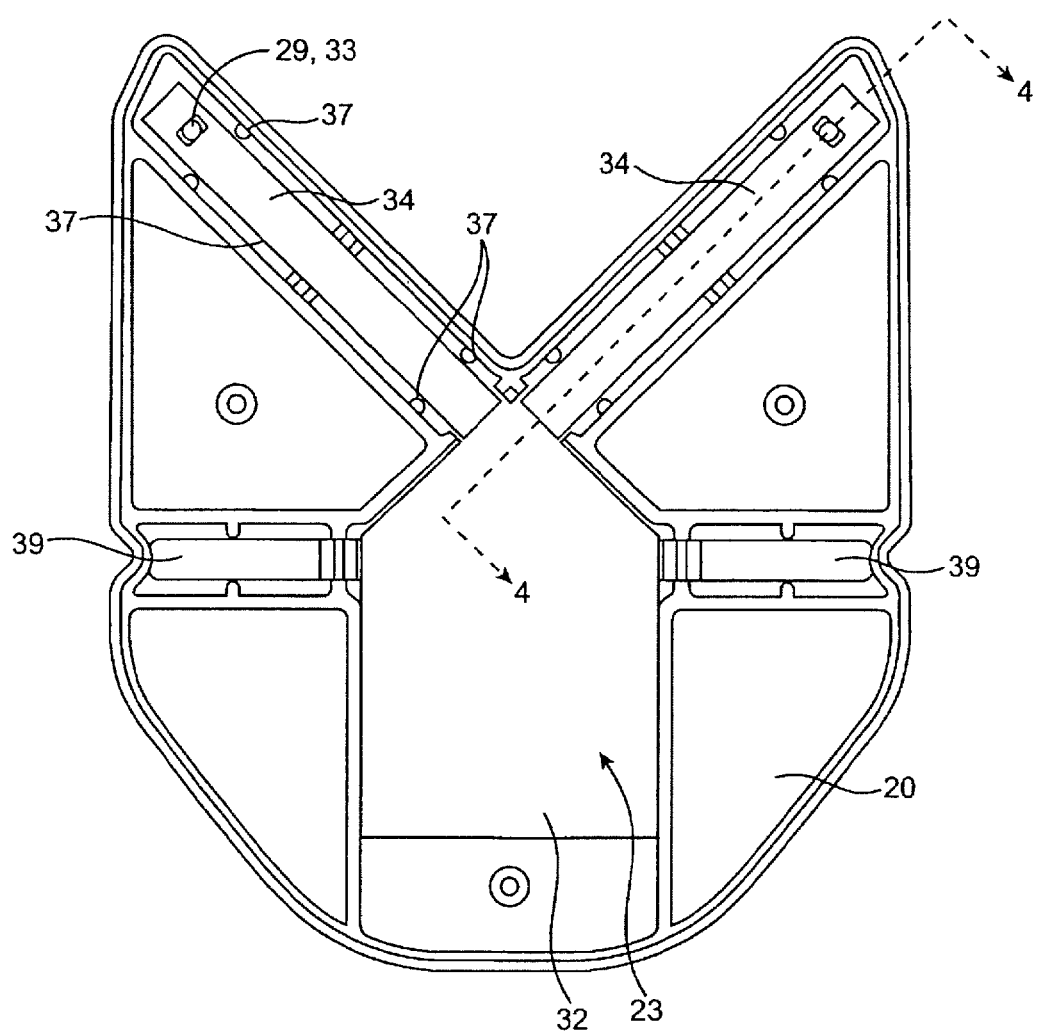
FIG. 3C corresponds to FIG. 3B, but includes a sample pad and a pair of test strips.

FIG. 3C shows the position of sample pad 32 and test strips 34 in bottom 20. As can be appreciated, when a fluid sample drops through hole 44 (in top 40, not shown) it is received directly onto sample receiving pad 32. From there, the sample wicks onto each of test strips 34. In addition, FIG. 3C shows a pair of autostart leads 39. Autostart leads 39 function to detect the presence of fluid sample on sample pad. Thus, autostart leads 39 can be used to activate the electronic and optical systems of a test meter. As a result, the present system can be activated (i.e.: "switched on") when a fluid sample is first detected on sample pad 32. One end of each of autostart leads 39 contacts sample pad 32. The other end of each of autostart leads 39 can be positioned adjacent to windows 19 (FIG. 3B) to make electrical contact to electrical system components in the test meter into which cartridge 30 is received.

Figure 4:
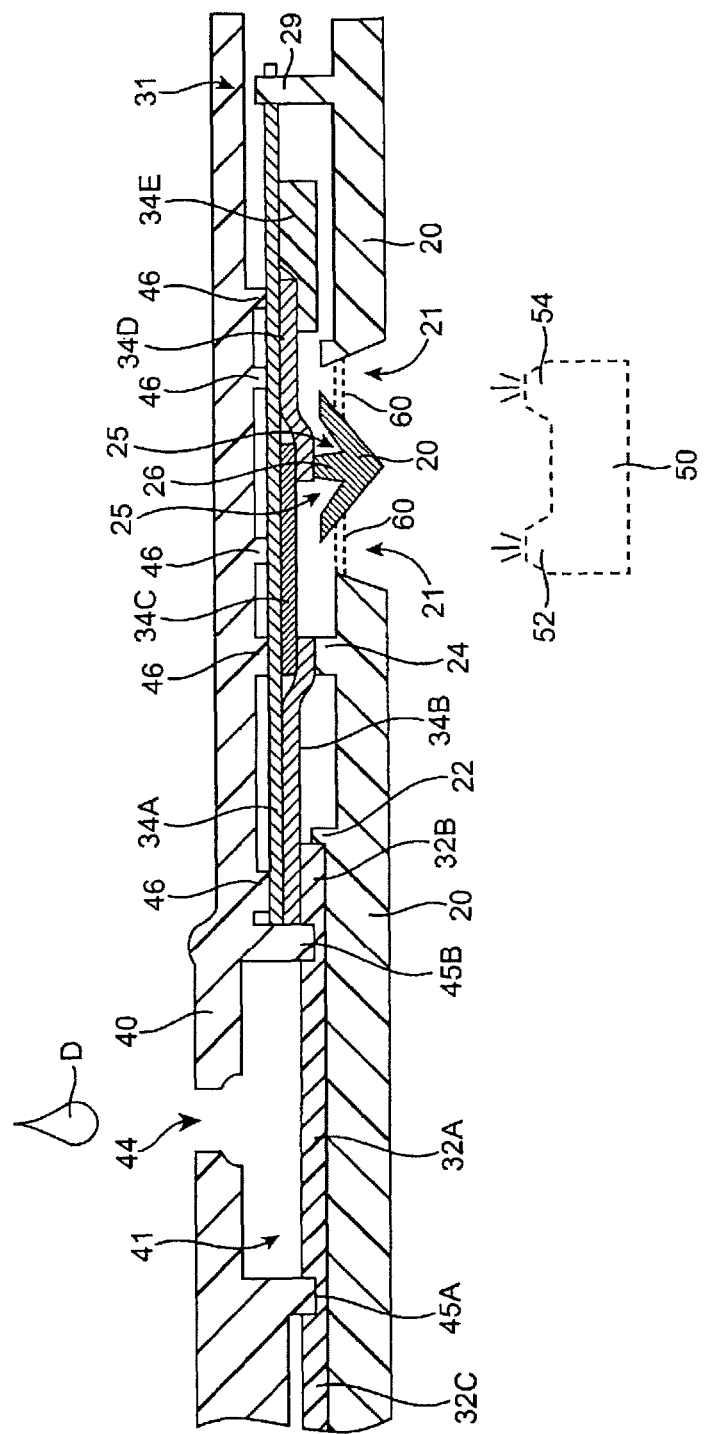
FIG. 4 is a sectional side elevation view along line 4-4 in FIGS. 2B and 3C (showing both the top and bottom of the cartridge positioned in relation to one another with the present fluid flow control features illustrated in detail).

FIG. 4 corresponds to a view taken along line 4-4 in FIGS. 2B and 3C showing the top 40 and bottom 20 of cartridge 30 with showing the top 40 and bottom 20 of cartridge 30 with sample pad 32 and a test strip 34 received therebetween. FIG. 4 illustrates the flow control features of the present invention in operation, as follows.

A fluid sample drop D (which may include a drop of blood, but is not so limited) is introduced through hole 44 in top 40. Drop D then reaches sample pad 32. In one embodiment, sample pad 32 is made of two layers of a non-woven absorbent cellulose-type material. However, sample pad 32 may be made of other suitable materials. In accordance with the present invention, the fluid sample then wicks from sample pad 32 into test strip 34 in a controlled manner, as follows.

As stated above, pinch wall 45A projects farther downwardly from top 40 than does pinch wall 45B. As a result, pinch wall 45A compresses sample pad 32 to a greater degree than pinch wall 45B. In one exemplary embodiment, pinch wall 45A compresses 60 to 90% of the height of sample receiving pad 32 and pinch wall 45B compresses 2 to 30% of the height of the sample receiving pad. In particular embodiments, pinch wall 45A compresses 70 to 80% of the height of sample receiving pad 32 and pinch wall 45B compresses 5 to 15% of the height of the sample receiving pad. It is to be understood that the above compression ranges are merely exemplary and that the exact compression ranges will depend upon the compressibility of the sample pad material, with more porous or open materials requiring higher compression.

As a result, fluid received into sample pad 32 (at portion 32A) has an easier time flowing under the bottom of pinch wall portion 45B (as opposed to flowing under pinch wall portion 45A). Therefore, when drop D initially reaches sample pad portion 32A (or when several drops D fill or partially fill chamber 41), the fluid will first pass under pinch wall 45B into sample pad portion 32B (i.e. the portion adjacent to test strip 34). From there, the fluid sample will wick into test strip 34. However, the speed of fluid movement is controlled by the presence of pinch wall 45B. Specifically, the presence of pinch wall 45B will advantageously prevent the fluid sample from simply flooding uncontrollably onto test strip 34, or otherwise splashing or leaking around in the interior of cartridge 30.

The excess fluid present in chamber 41 will then seep relatively slowly under pinch wall 45A into a rear portion 32C of sample pad 32, allowing test strip 34 to become sufficiently saturate, before a significant portion of the fluid has seeped into sample pad portion 32C. Rear portion 32C is preferably large enough such that it acts to absorb any excess fluid in chamber 41.

Due to the fact that pinch wall 45A compresses sample pad 32 to a greater degree than pinch wall 45B, fluid flow will occur as follows. Fluid will flow preferentially (i.e.: faster) from sample pad portions 32A to 32B and into test strip 34. Any excess fluid will flow from sample pad portion 32A at a slower rate into portion 32C, As a result, various sample volumes can be accommodated by the present invention, without the risk of flooding test strip 34, or having insufficient fluid flow enter test strips 34 in the first place.

Another feature of the present invention is its ability to control fluid flow through test strips 34 through the use of bottom support ribs 24 and 26 and top support ribs 46, as follows.

In preferred embodiments, test strip 34 has portions made of different materials. For example, test strip 34 may include a sheet of backing material 34A which may be made of a poly (ethylene terphthalate) (PET) such as white Mylar. Fluid does not flow through backing material 34A. A cellulose acetate portion 34B, a nitrocellulose portion 34C and a nylon portion 34D are all attached thereto. As can be seen, one end of cellulose acetate portion 34B is in overlapping contact with sample pad 32 and the other end of cellulose acetate portion 34B is in overlapping contact with nitrocellulose portion 34C. As can also be seen, one end of nylon portion 34D overlaps an end of nitrocellulose portion 34C and the other end of nylon portion 34D overlaps a sample absorbent pad 34E. In one optional embodiment of the invention, the measurement of HbA1c is carried out in test strip portion 34C, and the measurement of total Hb is carried out in test strip portion 34D. It is to be understood, however, that the present test strip design is merely exemplary. As such, other material(s) and assay tests may be substituted.

In accordance with the present invention, a top support structure (comprising support ribs 46) and a bottom support structure (comprising ribs 24 and 26) are used to control flow movement through test strip 34. Specifically, these support ribs ensure that flow passes sequentially through portions 34B, 34C, 34D and then into portion 34E in a manner that reduces the potential for capillary flow across the surface of test strip 34, or away from test strip 34 and into the housing of the device.

As can be seen, top support ribs 46 are spaced apart from one another and provide support at the locations where: (a) test strip portion 34B overlaps sample pad portion 32B, (b) where test strip portion 34B overlaps test strip portion 34C, and (c) where test strip portion 34D overlaps test strip portion 34C. At these locations, top support ribs 46 press the overlapping ends of the various test strip portions into contact with one another. This facilitates fluid transfer between the respective overlapping test strip portions. In addition, since top support ribs 46 are spaced apart and extend transversely across the top of test strip 34, top support ribs 46 also inhibit any potential fluid flow along the top surface of test strip 34.

Top support ribs 46 are also provided on top of test strip backing material 34A at locations where test strip portions 34C and 34D are exposed to apertures 21. These two top support ribs 46 assist in holding test strip portions 34C and 34D at an aligned location such that the reactions occurring therein can be accurately interrogated by an optical system 50. As illustrated, a first optical detector 52 is used to measure the reaction occurring on test strip portion 34C, and a second optical detector 54 is used to measure the reaction occurring on test strip portion 34D, In one preferred embodiment, optical system 50 is positioned within a reusable reflectance meter into which disposable cartridge 30 is received. It is to be understood, however, that the present invention is not so limited. For example, the present invention may also be used in a system in which test strips 34 are instead received within a disposable fluid analyte meter (i.e.: the optical system 50, sample pad 32 and test strip(s) are all incorporated into a single-use disposable fluid analyte meter).

Bottom rib 22 is used to assist in positioning sample pad 32 relative to test strip portion 34B. In preferred embodiments, bottom rib 22 does not contact test strip portion 34B. This is advantageous in that rib 22 acts as a fluid dam, preventing fluid seepage out of sample pad 32 and into the area under test strip 34. Thus, the potential for pooling of sample fluid between rib 22 and the surface of strip portion 34A is minimized. Bottom support rib 24 is used to press overlapping portions 34B and 34C of test strip 34 together. Thus, bottom support rib 24 controls the contact between portions 34B and 34C at their overlap point (by gently squeezing portions 34B and 34C together). As such, support rib 24 facilitates transfer of a diffusively absorbed material such as a colored latex from cellulose acetate portion 34B to nitrocellulose portion 34C. This prevents latex hang up in the overlap between test strip portions 34B and 34C. Similarly, bottom support rib 26 is used to press overlapping portions 34C and 34D of test strip 34 together, facilitating fluid transfer therebetween. Specifically, support rib 26 facilitates filtration of latex from the sample fluid and subsequent transfer of clarified fluid from nitrocellulose portion 34C to nylon portion 34D. Together, bottom support ribs 24 and 26 assist in facilitating fluid transfer between the respective overlapping test strip portions.

Bottom support ribs 24 and 26 raise test strip 34 off the inner surface of the cartridge (i.e.: away from bottom 20) thereby reducing the potential for "capillary bypass" flow (i.e. wherein the fluid sample migrates as a film over the bottom surface of strip 34 or between test strip 34 and into cartridge 30, rather than through the test strip matrix, as desired.) This prevents latex from bypassing the filtration site at the overlap between nitrocellulose portion 34C and nylon portion 34D. This is particularly advantageous in ensuring correct readings are taken through apertures 21 at test strip portions 34C and 34D.

In addition, bottom support ribs 24 and 26 work together with top support ribs 46 to ensure that test strip 34 is held at an aligned position such that when test strip 34 is received within the portion of the device formed by top chamber 48 (FIG. 2B) and bottom chamber 28 (FIG. 3B). In addition, the sides of test strip 34 do not contact the sides of chambers 28 and 48. In addition, four round guide pins 37 (FIG. 3C) can be used to contact the edges of test strip 34 to ensure that the edges of test strip 34 do not contact the sides of chambers 28 and 48. This assists in preventing any capillary fluid flow occurring in which fluid seeps away from the test strip 34 and into the body of the cartridge.

A further advantage of bottom support ribs 24 and 26 and top support ribs 46 extending fully across the top and bottom surfaces of test strip 34 is that they ensure that fluid flows evenly through test strip 34. Specifically, fluid will neither tend to flow faster or slower along through the middle of the test strip (as compared to the edges of the test strip). This advantageously restrains any left side/right side flow biases in test strip 34.

Figure 5:
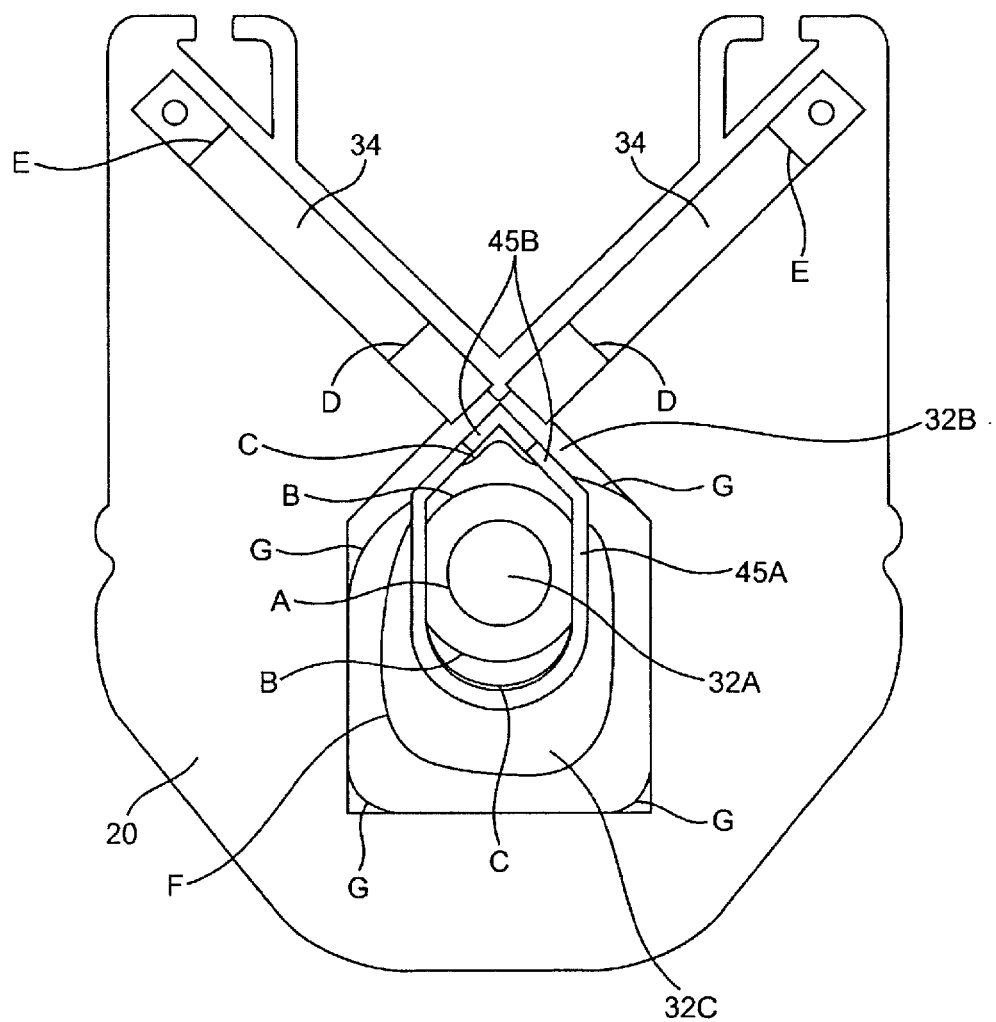
FIG. 5 is a schematic illustration of the sample receiving pad, test strips and pinch walls showing progressive movement of fluid flow over time in accordance with the present invention.

Turning next to FIG. 5, a schematic illustration of the sample receiving pad, test strips and pinch walls showing progressive movement of fluid flow over time in accordance with the present invention is provided.

A fluid sample is first received through top hole 44 onto sample pad portion 32A. The fluid sample first spreads across sample pad portion 32A to reach line A. With further filling of chamber 41, the fluid sample reaches line B, and then line C (filling or partially filling chamber 41 in FIG. 4). As stated above, pinch wall 45B only partially restrains the movement of the fluid sample thereunder, As a result, fluid will begin to seep under pinch wall portion 45B. As a further result, the fluid enters test strips 34 as a generally even front across test strips 34. Specifically, the fluid will tend to enter the left and right edges of test strips 34 at the same time that it enters the middle of each of test strips 34. This achieves a generally uniform flow from sample pad 32 onto test strips 34. Thereafter, the fluid will progress evenly through test strips 34, successively reaching lines D and then lines E. At this time, parallel reactions occur in the pair of test strips 34 between the fluid sample and the reagent preembedded or coating the test strips. At this time, test strips will become sufficiently saturated (due to continual seepage under pinch wall 45B maintaining sufficient saturation of sample pad portion 32B feeding fluid to test strips 34. Lastly, any excess fluid in pad portion 32A reaches line F and then line G in pad portion 32C.

The fluid sample on sample receiving portion 32A of sample pad 32 will seep under pinch wall 45A into sample pad portion 32C at a slower rate. As stated above, fluid will flow quicker under pinch wall 45B (i.e.: moving from sample pad portions 32A to 32B) and slower under pinch wall 45A (i.e.: moving from sample pad portions 32A to 32C). As a result, pinch wall 45A operates as an "overflow valve" such that the excess fluid on sample pad portion 32A is then directed away from test strip 34 (i.e.: into sample pad portion 32C). This action prevents flooding of test strips 34. This is particularly advantageous in that any excess fluid on test strips 34 could result in unwanted capillary bypass flow either: (a) along the top or bottom surfaces or edges of the test strip; or (b) away from the test strip and into other internal parts of cartridge 30.

The advantage of respective pinch wall portions 45A and 45B is that, by initially directing fluid towards test strips 34, they may provide sufficient saturation for consistent controlled release of a diffusively absorbent reagent in test strips 34. Such consistent controlled release of the reagent yields a high level of precision for the assay. Together, pinch walls 45A and 45B maintain sufficient saturation of the portion 32B of sample pad 32 feeding test strips 34. This ensures sufficient sample supply to consistently and completely release the latex from the cellulose acetate portion 34B of test strip 34, followed by an overflow means to control over saturation of test strip 34 once the latex has been released. Test strips that are over-saturated tend to be very shiny, giving noisy results when their reflectance is read. The present invention overcomes or considerably reduces this problem.

In various optional embodiments, support ribs 24 or 26 may be contoured to pinch unevenly across the various overlapping portions of test strip 34 so as to direct flow to the edges of the strip, or up the middle of the strip.

In various exemplary embodiments, test strip 34 comprises a reagent which reacts with a blood sample to yield a physically detectable change which correlates with the amount of selected analyte in the blood sample. Most preferably, the reagent on the test strip reacts with the blood sample so as to indicate the concentration of hemoglobin A1c (HbA1c). Examples of hemoglobin detection system are seen in U.S. Pat. Nos. 5,837,546 and 5,945,345, incorporated by reference herein in their entirety for all purposes. It is to be understood, however, that the present invention is not limited to using such reagents and reactions. Other analytic possibilities are also contemplated, all keeping within the scope of the present invention.

In one other optional aspect of the invention, a moisture barrier is provided in the housing of cartridge 30. This is shown in dotted lines in FIG. 4 as moisture barriers 60 covering apertures 21. Optional moisture barrier(s) 60 prevents moisture from entering the housing of cartridge 30, yet permits optical interrogation of test strip portions 34C and 34D therethrough. In optional aspects, moisture barrier 60 may filter out specific wavelengths of light to further enhance optical interrogation performance. The use of a sealed cartridge 30 with moisture barrier(s) 60 avoids the need for a dessicant to be placed within the device.

The invention claimed is:

1. A pinch wall system for controlling fluid flow movement from a sample receiving pad to a test strip, comprising:
    a sample receiving pad for receiving a fluid sample;
    a test strip in contact with the sample receiving pad; and
    a single pinch wall having a first section compressing said sample receiving pad and a second section compressing said sample receiving pad, said second section compressing said sample receiving pad to a lesser degree than said first section, said single pinch wall configured such that fluid flowing to said test strip flows past said second section whereby the flow is controlled.

2. The pinch wall system of claim 1, wherein the flow of fluid sample past said second section of said pinch wall is controlled so as to form a uniform front of fluid flow.

3. The pinch wall system of claim 1, wherein the flow of fluid sample past said second section of said pinch wall is controlled so as to form of consistent rate of fluid flow.

4. The pinch wall system of claim 1, wherein the sample receiving pad includes a bottom surface compressed by said pinch wall and said sample receiving pad includes a top surface for receiving a fluid sample.

5. The pinch wall system of claim 4, wherein said fluid flow past said second section is above said pinch wall.

6. The pinch wall system of claim 1, wherein said test strip comprises an upper surface, a lower surface, and a body between the upper and lower surfaces, the fluid sample being forced into the test strip body by said second section of said pinch wall.

7. The pinch wall system of claim 1, wherein said fluid sample forms a uniform front through said body.

8. The pinch wall system of claim 1, wherein said pinch wall contacts said sample receiving pad directly adjacent said test strip.

9. The pinch wall system of claim 1, further comprising:
    a second test strip in contact with the sample receiving pad;
    said single pinch wall having a third section compressing said sample receiving pad, the third section of said single pinch wall compressing said sample receiving pad to a lesser degree than said first section, said pinch wall configured such that all fluid flowing to said second test strip must flow past said third section of said single pinch wall;
    wherein the flow of fluid sample from said sample receiving pad to said second test strip is controlled by said third section of said single pinch wall.

10. The pinch wall system of claim 1, wherein said single pinch wall encircles a portion of said sample receiving pad to create a sample receiving portion and an overflow portion, the overflow portion being beyond said single pinch wall.

11. The pinch wall system of claim 10, wherein fluid may flow from said sample receiving portion to said overflow portion of said sample receiving pad.

12. The pinch wall system of claim 1, wherein the pinch wall is stationary with respect to the sample receiving pad while receiving the fluid sample and during the fluid flow.

* * * * *